(12) United States Patent
Montalbo et al.

(10) Patent No.: US 7,044,908 B1
(45) Date of Patent: May 16, 2006

(54) METHOD AND SYSTEM FOR DYNAMICALLY ADJUSTING FIELD OF VIEW IN A CAPSULE ENDOSCOPE

(75) Inventors: Joseph Domenick Montalbo, Menlo Park, CA (US); Gobi R. Padmanabhan, Sunnyvale, CA (US)

(73) Assignee: National Semiconductor Corporation, Santa Clara, CA (US)

( * ) Notice: Subject to any disclaimer, the term of this patent is extended or adjusted under 35 U.S.C. 154(b) by 359 days.

(21) Appl. No.: 10/615,761

(22) Filed: Jul. 8, 2003

(51) Int. Cl.
*A61B 1/04* (2006.01)
*A61B 1/06* (2006.01)

(52) U.S. Cl. ............... 600/160; 600/109; 600/177; 600/130; 600/173

(58) Field of Classification Search ............ 600/160, 600/178, 109, 176, 177, 173, 130, 129, 476; 348/65, 68
See application file for complete search history.

(56) References Cited

U.S. PATENT DOCUMENTS

| | | | |
|---|---|---|---|
| 5,603,328 A | | 2/1997 | Zucker et al. |
| 5,604,531 A | | 2/1997 | Iddan et al. |
| 6,057,909 A | | 5/2000 | Yahav et al. |
| 6,261,226 B1 * | | 7/2001 | McKenna et al. ......... 600/109 |
| 6,285,400 B1 * | | 9/2001 | Hokari ..................... 348/374 |
| 6,830,135 B1 * | | 12/2004 | Lin et al. ................... 190/115 |
| 6,895,270 B1 * | | 5/2005 | Ostrovsky ................. 600/476 |
| 2001/0035902 A1 | | 11/2001 | Iddan et al. |
| 2002/0032366 A1 | | 3/2002 | Iddan et al. |
| 2002/0109774 A1 | | 8/2002 | Meron et al. |
| 2003/0117491 A1 * | | 6/2003 | Avni et al. ................... 348/77 |
| 2003/0130562 A1 * | | 7/2003 | Barbato et al. ............ 600/109 |
| 2003/0171653 A1 * | | 9/2003 | Yokoi et al. ............... 600/160 |
| 2003/0195415 A1 * | | 10/2003 | Iddan ....................... 600/424 |
| 2004/0092825 A1 * | | 5/2004 | Madar et al. .............. 600/473 |
| 2004/0249245 A1 * | | 12/2004 | Irion ......................... 600/160 |

OTHER PUBLICATIONS

Astaras, Alexander et al., Dec. 4-7, 2002, "A Miniature Integrated Electronics Sensor Capsule for Real-Time Monitoring of the Gastrointestinal Tract (IDEAS)." ICBME 2002: "The Bio-Era: New Challenges, New Frontiers."
Lin, Gisela and William Tang, May 20, 2004, "Wearable Sensor Patches for Physiological Monitoring," pp. 1-2. Can be found at http://www.nasatech.com/Briefs/Feb00/NP020651.html.

(Continued)

*Primary Examiner*—John P. Leubecker
(74) *Attorney, Agent, or Firm*—John W. Branch; Darby & Darby PC

(57) ABSTRACT

A capsule endoscope (CE) having a field of view that may be dynamically adjusted. The CE includes an illuminator that may be an optical or acoustical illuminator designed to illuminate the lining of a GI tract. A scanner, such as a MEMS scanner may be used to scan the illumination source onto the lining. The scanner may be controlled to dynamically adjust the field of view. A lenslet array may also be used to focus the illumination. The sensor is formed such that it may be curved to a contour and includes a support having sufficient flexibility such that it can be formed to the contour. The substrate includes the sensor and is formed sufficiently thin so that it can be shaped to the contour. The substrate is coupled with the support such that the combination can be formed to the contour.

21 Claims, 6 Drawing Sheets

OTHER PUBLICATIONS

Lin, Gisela et al., May 20, 2004, "Improved Sensor Pills for Physiological Monitoring," pp. 1-2. Can be found at http://www.nasatech.com/Briefs/Feb00/NP020652.html.

U.S. Appl. No. 10/281,836, filed Oct. 28, 2002, Mohan Yegnashankaran.

* cited by examiner

METHOD AND SYSTEM FOR DYNAMICALLY ADJUSTING FIELD OF VIEW IN A CAPSULE ENDOSCOPE

FIELD OF THE INVENTION

The present invention is related to electronic sensors for capsule endoscopes, and more specifically to adjusting the field of view for a capsule endoscope.

BACKGROUND OF THE INVENTION

Endoscope inspection is a tool commonly used in detecting gastro-intestinal (GI) diseases. As the endoscope proceeds through the GI tract sensor readings may be obtained to detect the abnormalities.

The endoscope inspection may utilize many different sensors to observe and detect abnormalities within the GI tract. These sensors may include imaging sensors, temperature sensors, pH sensors, as well as other types of sensors.

One such endoscope tool is a capsule that is swallowed by the patient. For many of the patients the capsule moves through the GI tract within a twenty-four hour period. An advantage of the endoscope capsule is that during the GI inspection the patient is generally not hooked up to external machinery. There are many disadvantages; however, that are associated with the capsule.

One disadvantage is that it is difficult to configure the sensors for the capsule. As the capsule size is small, space is at a premium making the configuration of the sensors important. What is needed is a way to more efficiently configure the sensors associated with the capsule.

SUMMARY OF THE INVENTION

Briefly described, the present invention is directed at providing a capsule endoscope (CE) having a field of view that may be dynamically adjusted.

According to one aspect of the invention, the CE includes an illuminator that may be an optical or acoustical illuminator designed to illuminate the lining of a GI tract.

According to another aspect of the invention, a scanner, such as a MEMS scanner may be used to scan the illumination source onto the lining of the GI tract. The scanner may be controlled to dynamically adjust the field of view.

According to yet another aspect of the invention, a lenslet array is used to focus the illumination.

According to yet another aspect, the sensor is formed such that it may be curved to a contour and includes a support having sufficient flexibility such that it can be formed to the contour. The substrate includes the sensor and is formed sufficiently thin so that it can be shaped to the contour. The substrate is coupled with the support such that the combination can be formed to the contour.

DETAILED DESCRIPTION OF THE PREFERRED EMBODIMENT

Figure 1:
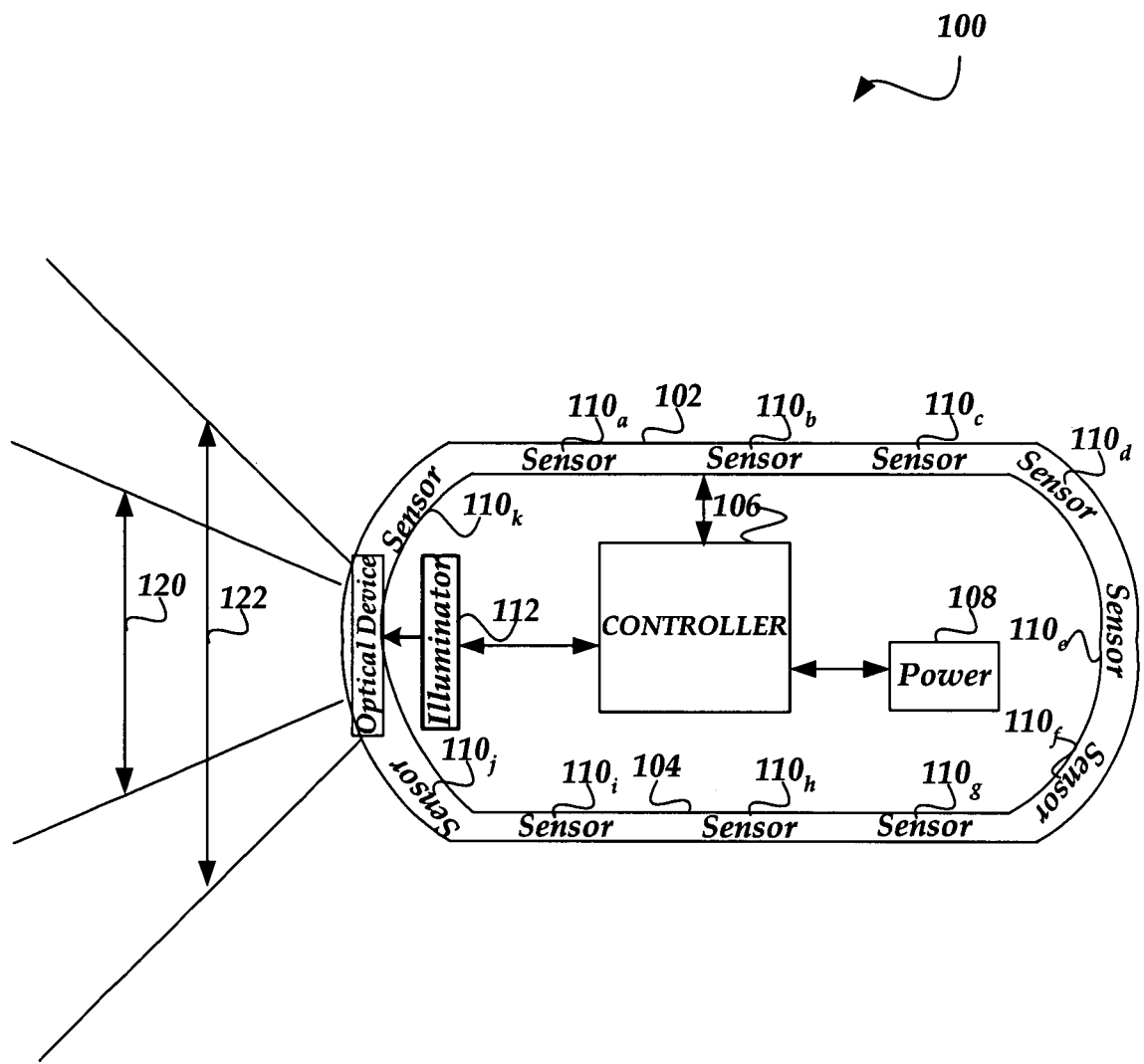
FIGS. 1 and 2 show a schematic diagram of a capsule endoscope having an exemplary sensor configuration.

In the following detailed description of exemplary embodiments of the invention, reference is made to the accompanied drawings, which form a part hereof, and which is shown by way of illustration, specific exemplary embodiments of which the invention may be practiced. These embodiments are described in sufficient detail to enable those skilled in the art to practice the invention, and it is to be understood that other embodiments may be utilized, and other changes may be made, without departing from the spirit or scope of the present invention. The following detailed description is, therefore, not to be taken in a limiting sense, and the scope of the present invention is defined only by the appended claims.

Throughout the specification and claims, the following terms take the meanings explicitly associated herein, unless the context clearly dictates otherwise. The meaning of "a," "an," and "the" includes plural reference, the meaning of "in" includes "in" and "on." The term "connected" means a direct electrical connection between the items connected, without any intermediate devices. The term "coupled" means either a direct electrical connection between the items connected or an indirect connection through one or more passive or active intermediary devices. The term "circuit" means either a single component or a multiplicity of components, either active and/or passive, that are coupled together to provide a desired function. The term "signal" means at least one current, voltage, or data signal. Referring to the drawings, like numbers indicate like parts throughout the views.

The terms "comprising," "including," "containing," "having," and "characterized by," mean an open-ended or inclusive transitional construct and does not exclude additional, unrecited elements, or method steps. For example, a combination that comprises A and B elements, also reads on a combination of A, B, and C elements.

The term "endoscope" means a small, flexible tube with a light and a lens on the end. It can be used to look into the gastrointestinal (GI) tract of a patient, e.g., the esophagus, stomach, duodenum, colon, or rectum. It can also be employed to take tissue from the GI tract for testing, to provide therapeutic drugs to a particular location in the GI tract, and to take color photographs of the inside of the body. There are many types of endoscopes, including, but not limited to, colonoscopes and sigmoidoscopes.

The term capsule endoscope (CE) means a "capsule" or "pill" shaped diagnostic device for observing characteristics in the lining of the GI tract of a patient although various shapes may be employed. The CE is orally administered and may be propelled by peristalsis to move throughout the entire length of the gastrointestinal tract where it is eventually excreted by the patient. In one embodiment, the capsule endoscope can produce images of the internal lining of the GI tract either along its entire length or at sections of particular interest to medical professionals. The images may be stored in the capsule endoscope or broadcast to a receiver outside the body. The images may be illuminated by various wavelengths of light (both visible and non-visible as well as other forms of electromagnetic radiation such as X-rays) by sources included in the capsule endoscope. The images may also be illuminated using acoustic signals.

Other embodiments of the capsule endoscope may be arranged to measure temperature, pH level, or any other characteristic of the GI tract. Some embodiments of the capsule endoscope may be arranged to enable an operator to control the movement of the capsule endoscope along the GI tract, other embodiments may be configured to enable the capsule endoscope to take a biopsy of the lining of the GI tract, and still other embodiments may be arranged to enable the capsule endoscope to provide a therapeutic treatment to a particular location in the GI tract.

Additionally, although a CE is not intended to be limited to the particular "shape" or size of a capsule, one embodiment of the capsule endoscope could have an elongated "capsule" shape with dimensions of approximately 11 millimeters by 26 millimeters.

The invention is directed to providing a sensor configuration for dynamically adjusting a field of view for a CE that is employed to observe characteristics in the lining of the gastrointestinal tract of a patient. As mentioned elsewhere, these characteristics can be images, temperature, pH level and the like. The CE is arranged such that the sensors may be formed as part of the capsule shell, or formed to follow the contours of the shell.

FIG. 1 shows a schematic diagram of a capsule endoscope including an exemplary sensor configuration, in accordance with aspects of the invention. Exemplary capsule endoscope (CE) 100 is "capsule" shaped and sized for oral administration to a patient. Several components are disposed inside CE 100 including controller 106, which is coupled to power 108. Controller 106 is configured to control operation of the sensors, illuminators, and other devices that may be contained within the CE. According to one embodiment, sensors $110_{a-k}$ are disposed along the outer surface of CE 100 and may form the shell of CE 100. Illuminator 112 is positioned to provide illumination to a scene to be viewed by the CE. More specifically, illuminator 112 provides a signal used for illuminating the lining of a patient's gastrointestinal tract and sensors $110_{a-k}$ are configured to collect data. The illumination may be optic and/or acoustic. For example, at least one of the sensors may be an imager to capture images of the illuminated lining. Additionally, an illuminator may provide light of a selected wavelength that is most suited to observing a particular characteristic of the lining of the patient's gastrointestinal tract. Other sensors may be configured to measure pH level, temperature, and the like.

According to one embodiment, an illuminator is coupled to an optical device that is configured to dynamically change the field of view. The optical device may comprise many different devices. For example, the optical device may be a scanner, such as a MicroElectroMechanical Systems (MEMS) scanner. The scanner may be dynamically controlled by controller 106 and adjusted to change the field of view as is illustrated by field of view 120 and field of view 122. The optical device may consist of other devices like, optical lenses, or lenslet arrays to focus the illumination source. The lenslet array may be configured to have a spatially varying focal length beneficial when used with a scanner. This type of lenslet array produces focal spots falling on a cylinder allowing parallel scanning of a curved surface. Many other types of lenslet arrays may be used depending on the application. For example, a diffractive lenslet array may be used for illuminating a specific pattern on the scene. The illuminator is not limited to optical illumination but may also be acoustical. For example, the illuminator may be an emitter of various electromagnetic wavelengths as well as an ultrasound illumination device. Illuminators and optical devices may be placed in other locations of CE 100 as determined by the desired application. The sensors may also be configured to activate in response to the selected field of view. For example, more sensors may be implemented to image an area having a large field of view as compared to image a smaller field of view.

An outer shell coating (not shown) may be disposed over the other sensors to provide protection to CE 100. Also, at least a portion of the outer surface of CE 100 may be coated with a medicine, such as heparin, to prevent clotting, and the like. The outer surface of CE 100 may be manufactured or coated from materials that are known to be biologically inert, such as plastic, nylon, composite, stainless steel, and the like.

In another embodiment (not shown), a lens and/or a filter may enable at least one of the sensors (110) to capture different resolutions and/or aspects of images such as color of the lining of a patient's gastrointestinal tract.

Figure 2:
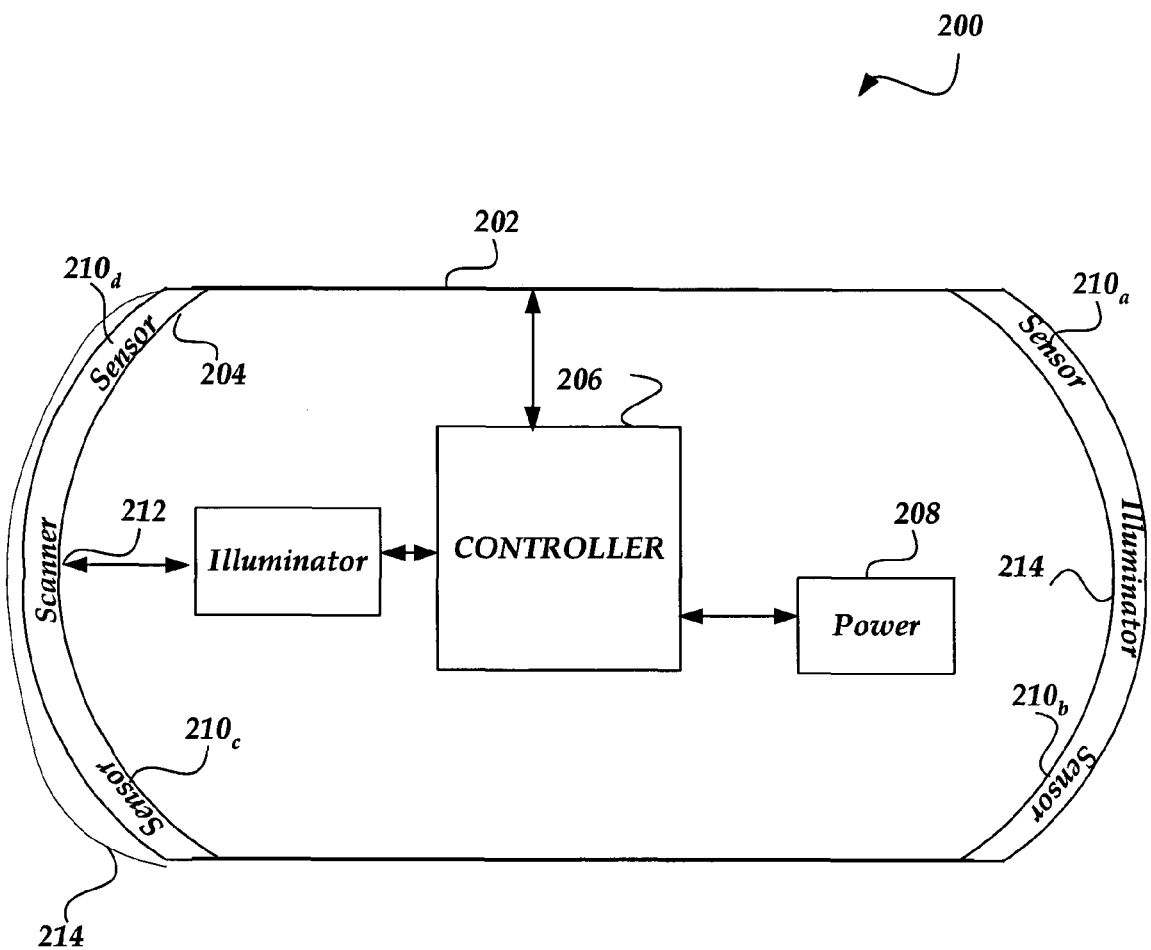

FIG. 2 illustrates a schematic of a capsule endoscope wherein a portion of the shell includes an exemplary sensor configuration, in accordance with aspects of the present invention. FIG. 2 is similar to FIG. 1 but includes an illuminator source and a scanner on a portion of the shell of the CE.

As shown in the figure, CE 200 includes sensors $210_{a-d}$ along the ends of the CE. Sensors may form any portion of the CE. Alternatively, or in addition, the sensors may be formed to match the contour of the shell 214 of the CE. Additionally, the sensors may include active electronic devices, such as illuminators, transmitters, and the like.

One aspect of the invention includes the fabrication and implementation of a CE shell having a curved surface including sensors. Embodiments of the invention contemplate sensors where the configuration of the curved surface of the sensors substantially matches that of the capsule that the sensor is attached or form. One such embodiment is discussed with respect to FIG. 3B.

Figure 3A:
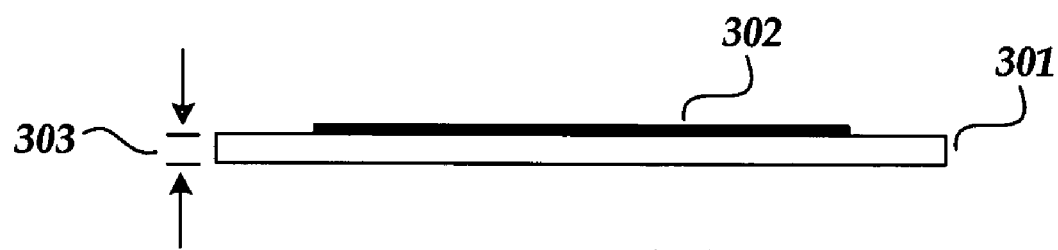
FIGS. 3(a) and 3(b) are cross-section views of a flexible semiconductor substrate and the relationship of such a substrate to a capsule endoscope shell.

FIG. 3A depicts an embodiment of a sensor configuration for a CE constructed in accordance with the principles of the present invention. For purposes of discussion, the exemplary sensor illustrated is an imaging sensor. Other types of sensors (or active electronic devices such as illuminators) may be constructed using the same methodology. Sensor 300 comprises a semiconductor substrate 301 having an array of optical elements 302 formed on its top surface. Suitable semiconductor substrate materials include, but are not limited to, silicon (Si), gallium arsenide (GaAs), gallium indium arsenide (GaInAs). These substrate materials may include other semiconductor materials. The optical elements 302 are formed on the top surface of the substrate 301. Such optical elements commonly include arrays of electronic photo-detector circuitry. The elements can include arrays of photodiodes, charge coupled devices (CCD's), CMOS devices, and numerous other light sensitive optical detectors. The devices can be accompanied or replaced by other optical elements including, but not limited to filters, blockers, and reflectors. Additionally, the principles of the present invention can be applied to other sensors beyond photo imaging devices.

Semiconductor substrate 301 is formed having a substantially reduced thickness 303 when compared to substrates of ordinary thickness. A suitable substrate thickness is on the order of about 25 microns to about 125 microns thick. Such a thin substrate 301 imparts flexibility to substrate 301 while retaining sufficient strength so as to not break when flexed over various angles of curvature. The thinness and flexibility enables substrate 301 to be flexed or bent to obtain a desired surface contour. As such, substrate 301 may be formed to the desired shape of the capsule endoscope shell. The substrate may form the entire CE shell or a portion of the CE shell. Alternatively, the substrate may be contoured to substantially match the contours of the CE shell.

Figure 3B:
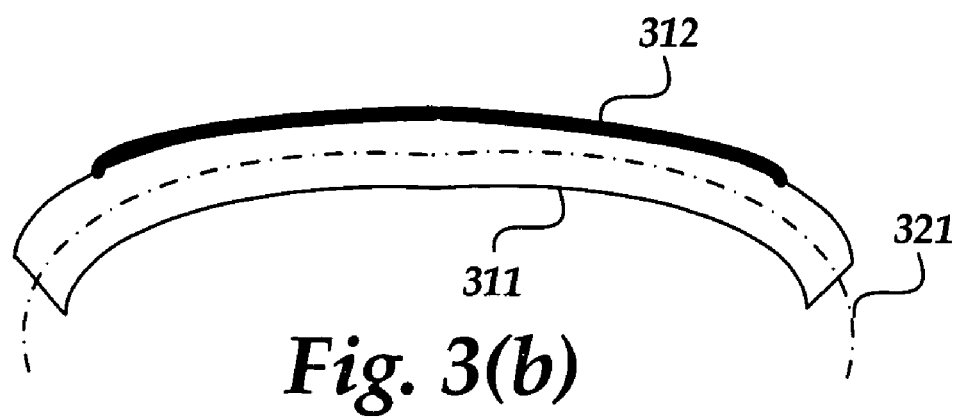

FIG. 3(b) depicts an appropriately thin semiconductor substrate 311 flexed into a curved configuration that substantially conforms to form the shell of a CE. In this way, elements 312 of the sensor may be flexed to match the contour of a CE.

FIGS. 4(a)–4(d) schematically depict an exemplary sensor embodiment and a method embodiment for its fabrication. In the embodiment schematically depicted in FIG. 4(a), a standard semiconductor wafer 401 is shown with a plurality of photo-sensitive detector elements 402 formed on a surface of the wafer. In one example, wafer 401 can be a conventional silicon wafer about 750µ thick, constructed in accordance with ordinary manufacturing processes. According to one embodiment, sensor elements 402 are photoimager arrays. Other optical or electro-optical components, or other sensor elements, can also be formed on the surface. The sensors formed on the surface may be many types of sensors, including sensors for temperature, pH, infrared, and the like. The sensor elements 402 of the depicted embodiment are formed into photoimager arrays in accordance with conventional fabrication techniques.

Figure 4A:
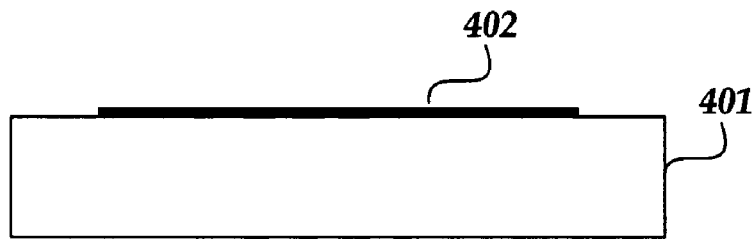
FIGS. 4(a)–4(d) are cross-section views of a portion of a semiconductor substrate showing a process embodiment used for fabricating flexible substrates.
Figure 4B:
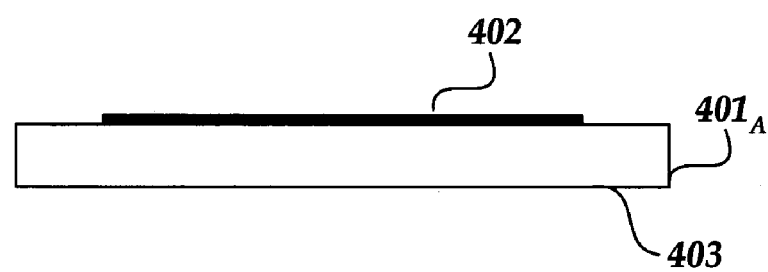
Figure 4C:
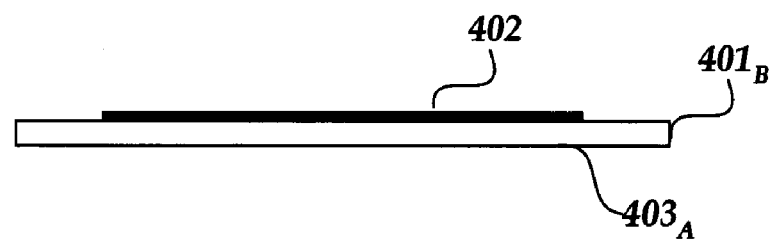

As depicted in FIG. 4(b), the wafer is subjected to a bulk back-grinding process using any one of a number of conventional back-grinding processes. Portions of the backside surface 403 of wafer $401_A$ are removed to produce the resulting embodiment depicted in FIG. 4(b). In one embodiment, the backside surface is subjected to chemical mechanical polishing (CMP) to remove material from the backside of the wafer. Other methods of bulk material removal can also be used to remove material from the backside of the wafer. Typically, such back-grinding proceeds until the wafer is on the order of about 125µ to about 175µ thick. One preferred thickness is on the order of about 150µ thick.

The wafer is then subjected to precision removal of backside material to reach a final desired thickness. In one embodiment depicted in FIG. 4(c), "plasma back-grinding" can be used to remove portions of the backside surface $403_A$ of wafer $401_B$. Such precision removal of backside material continues until the wafer $401_B$ is about 25µ to about 100µ thick. The actual thickness is dependent on the wafer material and the degree of flexibility and curvature desired in the final substrate. Some portions of the substrate may be thinner than other portions of the substrate. Many processes can be used to achieve precision removal of material from the backside surface $403_A$ of the wafer $401_B$. In one embodiment, atmospheric downstream plasma (ADP) etching is used to thin wafers $401_B$ by precision removal of backside material. In one example process, a wafer having been subjected to bulk back-grinding is placed in a process chamber of an ADP etch system. For example, a TE-2001 series ADP machine available from Tru-Si Technologies of Sunnyvale, Calif. can be used. An argon flow of about 1 standard liter per minute (slm) is supplied along with a gas flow of suitable fluorine containing gases. Examples of suitable fluorine containing gases include $CF_4$, $SF_6$, as well as other fluorine containing gases. Suitable gas flow rates for the fluorine containing gases are about 4 slm to about 6 slm, but may vary with gas type chosen as well as other process needs. Such precision removal of backside material continues until the wafer $401_B$ obtains the desired thickness.

One advantage of such precision removal of material (especially; when accomplished using plasma etching techniques) is that stresses induced during bulk back-grinding are relieved by such precision removal of material from the backside surface. Plasma etching does not induce stresses in the wafer. Another advantage of such precision removal of material (especially, with plasma etching) is that it can obtain extremely precise wafer thicknesses for the wafer $401_B$.

Figure 4D:
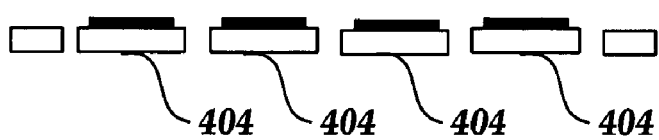

In FIG. 4(d), the wafer is shown after singulation into a plurality of separate individual photoimager dies 404. Each die includes an image sensor.

Figure 5A:
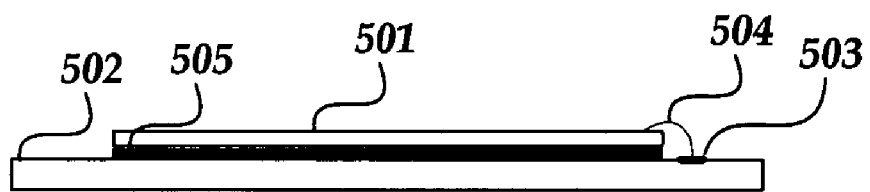
FIG. 5(a) is a cross-section view of a flexible substrate mounted on a flexible support.

Referring to FIG. 5(a) the forgoing embodiment can be further expanded upon. Flexible substrate 501 is coupled with a flexible support 502. Support 502 provides a flexible support that increases the robustness of substrate 501. In one embodiment, support 502 can be formed of a polyimide material. Also, a laminated support 502 can be constructed having alternating layers of copper and polyimide materials. Many sufficiently flexible materials can be used as a support 502. An adhesive can be used to couple substrate 501 with flexible support 502. In one example, an epoxy layer 505 about 20µ to about 30µ thick can be used to attach substrate 501 with flexible support 502. Many other approaches for coupling substrate 501 with the flexible support 502 may be used. Also, support 502 can provide contact surfaces for electrical connections. In the depicted embodiment, support 502 includes bonding surfaces 503 that can be electrically coupled to the circuitry of substrate 501. For example, bonding surfaces 503 can be wire-bonded to substrate 501 using connector wires 504.

Figure 5B:
FIG. 5(b) is a cross-section view of an embodiment of a sensor module employing a flexible substrate mounted on a flexible support.

FIG. 5(b) depicts one embodiment of a CE incorporating a sensor module 510 as part of its shell. For example, using support 502 and substrate 501 of FIG. 5(a), the electrical connections are encapsulated by protective layer 506 (e.g., a moisture resistant epoxy). Support 502 and substrate 501 are curved into a contour that matches the desired contour, such as the surface of a CE shell.

Figure 6:
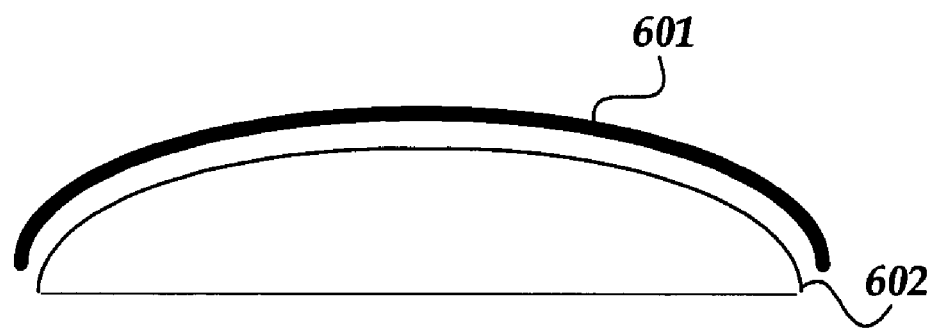
FIG. 6 is a view of a rigid support having a preformed mounting surface with a curved mounting surface.

FIG. 6 shows a view of a rigid support having a preformed mounting surface with a curved mounting surface, in accordance with aspects of the present invention. This embodiment makes use of a rigid support structure (602) having a curved surface portion of the rigid support. Embodiments can assume a number of different shapes. Such rigid supports can be formed of a multitude of different materials including, but not limited to ceramics and plastics.

According to one embodiment, a CE shell (such as illustrated in FIG. 1 and FIG. 2) may be formed by a flexible substrate, in accordance with aspects of the present invention. The sensor circuitry (e.g., a photo detector array, illuminator, and the like) may be formed on a surface of the substrate. The substrate with the sensor circuitry may be coupled with a rigid support or a flexible support. The surface contour of the curved surface portion is configured so that the substrate may be fitted onto the curved surface portion of CE, or form the shell of the CE. In the depicted implementation, the substrate is coupled with a support using an adhesive. For example, an epoxy layer about 20µ to about 30µ thick can be used to attach the substrate with the support. Other coupling approaches may be used to couple the substrate.

The support and substrate may be mounted inside a protective housing. The housing may include an optically transmissive surface (or window) through which light can pass onto the sensor circuitry. The optically transmissive surface may be configured to allow visible wavelengths as well as non-visible wavelengths to pass onto the sensor circuitry. Optical devices can be mounted above the sensor circuitry at a desired optical distance from sensor circuitry thereby optically coupling the devices with the sensor circuitry and completing an optical imaging module.

Figure 7:
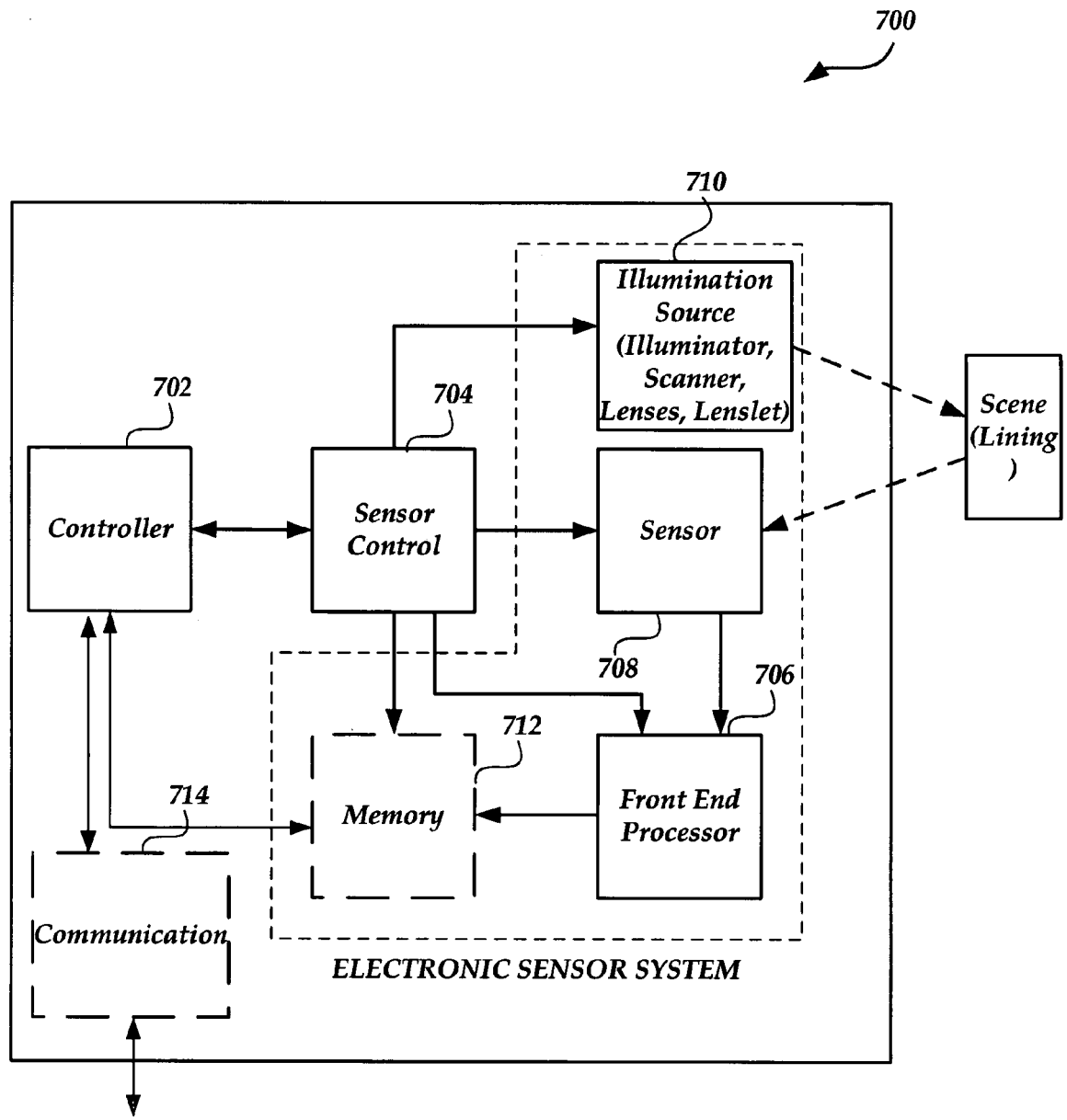
FIG. 7 is an exemplary sensor system; in accordance with aspects of the present invention.

FIG. 7 is an illustrative system diagram that is arranged in accordance with aspects of the present invention. Sensor system 700 includes a sensor control block and an electronic sensor system block.

The sensor processing block may include processing unit (e.g., micro-processor, micro-controller, computer, etc.) that is configured to analyze the sensor data. The sensor data can be processed for brightness and contrast adjustment, as well as other functions such as edge detection, image recognition, and the like.

Optional communication interface 714 is configured to act as a receiver and a transmitter. The receiver is arranged to receive signals from a wireless communication channel. The transmitter is arranged to transmit sensor data to an external control unit (not shown) through the wireless communication channel. The signals are received by the sensor control block (704) through controller 702, which controls timing and processing for the electronic sensor system and the communication interface.

The electronic sensor system includes blocks for an illumination source (710), a sensor or sensor array (708), a front end processor (706), and an optional memory (712). Illumination source 710 is activated and deactivated by the sensor controller block (704) to control illumination of a scene. The sensor block (e.g., a pixel array) processes the signal that is reflected from the scene when activated by the sensor control block. Image sense signals are provided to the front end processor block by the sensor. The front end processor block is configured to adjust the image sense signals for parameters such as offset and gain. The processed image sense signals are either stored in the optional memory block, or transmitted to the external control unit as image data.

The illumination source may include a scanner and other optical devices, such as a lenslet array (as discussed in FIG. 1) configured to illuminate a field of view. The illumination source is controlled by the sensor control. Sensor control may provide instructions to the illuminator source to change the range of the scanner, or the intensity level of the source.

The sensor block may be configured as a pixel sensor array that is arranged as a series of pixel sensors that are organized in rows and columns. Each row of pixel sensors is selected for processing by a row control signal. Each pixel sensor provides an output signal to a column line when selected. Each column line is processed by the column and scan control block to provide a sensor signal to the front end processor block.

The pixel sensor array may be a passive array or an active array. The timing of the activation and scanning of the various pixels is determined by the sensor control block. For example, the sensor control block activates a row select signal via the row control block when the pixel sensor array is exposed by illumination reflected from a scene. The reflected illumination results in the accumulation of photocarriers in each exposed pixel. The accumulated photocarriers result in a charge that is related to the total integration time and the illumination level of the reflected singal from the scene. The column line is selected to scan the sensed signal after the integration time (the exposure time interval) has been terminated by the sensor control block.

The above specification, examples and data provide a complete description of the manufacture and use of the composition of the invention. Since many embodiments of the invention can be made without departing from the spirit and scope of the invention, the invention resides in the claims hereinafter appended.

We claim:

1. A capsule endoscope (CE) having a field of view that may be dynamically adjusted, comprising:
   an illuminator configured to produce illumination;
   an optical device configured to transmit the illumination onto a lining of a GI tract;
   a sensor that is arranged to sense a reflected signal from the lining in response to the illumination and to provide signals relating to the reflected signal;
   a control block coupled to the illuminator that is configured to dynamically adjust the field of view of the illumination;
   wherein the sensor is curved to a contour and includes:
      a support having sufficient flexibility such that it is formed to the contour;
      a substrate including the sensor; the substrate being formed sufficiently thin so that it is shaped to the contour; and
      the substrate coupled with the support such that the combination is formed to the contour.

2. The CE of claim 1, wherein the optical device comprises a scanner configured to scan the illumination onto the lining.

3. The CE of claim 2, wherein the scanner comprises a MEMS scanner.

4. The CE of claim 2, wherein the optical device comprises a lenslet array configured to focus the illumination.

5. The CE of claim 1, wherein the illuminator comprises an optical illuminator.

6. The CE of claim 1, wherein the illuminator comprises an emitter for an acoustical signal.

7. The CE of claim 1, further comprising a communication interface that is arranged to transmit and receive signals relating to the lining over a wireless communications link.

8. The CE of claim 1, wherein the support and substrate are arranged inside a protective housing.

9. The CE of claim 8, wherein the protective housing includes a portion of an optically transmissive surface.

10. The CE of claim 9, further comprising a lenslet covering the sensor.

11. The CE of claim 8, wherein the substrate includes a silicon material.

12. A method for dynamically adjusting a field of view for a CE having sensors that may be formed to follow a contour associated with the CE; comprising:
   producing illumination;
   transmitting the illumination onto a lining of a GI tract;
   sensing a reflected signal from the lining in response to the illumination and providing signals relating to the reflected signal;
   dynamically adjusting the field of view;
   forming the sensors; wherein forming the sensors comprises:
      bulk removing substrate material from the back side of a substrate; and
      precision removing substrate material from the back side of the substrate until the substrate has a desired thickness that enables the sensors formed on the substrate to be flexed and shaped into a curved configuration.

13. The method of claim 12, wherein transmitting the illumination onto the lining of a GI tract further comprise scanning the illumination onto the lining.

14. The method of claim 13, wherein scanning the illumination further comprises using a MEMS scanner.

15. The method of claim 14, further comprising focusing the illumination using a lenslet array.

16. The method of claim 12, wherein producing the illumination further comprises producing the illumination using an optical illuminator.

17. The method of claim 12, wherein producing the illumination further comprises producing the illumination using an acoustical illuminator.

18. The method of claim 12, further comprising transmitting and receiving signals relating to the lining over a wireless communications link.

19. The method of claim 12, further comprising coupling the substrate to a support.

20. The method of claim 19, wherein the support is selected from a flexible support and a rigid support.

21. A capsule endoscope (CE) having a field of view that is dynamically adjustable, comprising:

an illuminator configured to produce illumination;

a device that is adapted to transmit the illumination onto a lining of a gastrointestinal tract;

a sensor that is arranged to sense a reflected signal from the lining in response to the illumination and to provide at least one signal regarding the reflected signal; and a control block configured to dynamically adjust the field of view, wherein the sensor is curved to a contour and includes:

a support having sufficient flexibility such that it is formed to the contour; and a substrate including the sensor, wherein the substrate is sufficiently thin so that it is shaped to the contour.

* * * * *

UNITED STATES PATENT AND TRADEMARK OFFICE
CERTIFICATE OF CORRECTION

| | | |
|---|---|---|
| PATENT NO. | : 7,044,908 B1 | |
| APPLICATION NO. | : 10/615761 | |
| DATED | : May 16, 2006 | |
| INVENTOR(S) | : Joseph Domenick Montalbo et al. | |

It is certified that error appears in the above-identified patent and that said Letters Patent is hereby corrected as shown below:

Title Page, Col. 2 (Other Publications), Line 8, Delete "NP020651.html." and insert --NP020652.html. --.

Column 2, Line 10, Delete "EMBODIMENT" and insert -- EMBODIMENTS --.

Signed and Sealed this

Twenty-first Day of November, 2006

JON W. DUDAS
*Director of the United States Patent and Trademark Office*